United States Patent [19]

Kamen

[11] Patent Number: 5,222,946
[45] Date of Patent: Jun. 29, 1993

[54] COMPACT INTRAVENOUS FLUID DELIVERY SYSTEM

[75] Inventor: Dean L. Kamen, Bedford, N.H.

[73] Assignee: Deka Products Limited Partnership, Manchester, N.H.

[21] Appl. No.: 795,880

[22] Filed: Nov. 21, 1991

Related U.S. Application Data

[63] Continuation-in-part of Ser. No. 792,877, Nov. 15, 1991, and a continuation-in-part of Ser. No. 792,483, Nov. 15, 1991, and a continuation-in-part of Ser. No. 673,835, Mar. 22, 1991, abandoned, and a continuation-in-part of Ser. No. 615,612, Nov. 19, 1990, abandoned, and a continuation-in-part of Ser. No. 614,806, Nov. 19, 1990, abandoned, which is a continuation-in-part of Ser. No. 523,801, May 15, 1990, Pat. No. 5,088,515, and a continuation-in-part of Ser. No. 345,387, May 1, 1989, Pat. No. 4,976,162, which is a continuation-in-part of Ser. No. 92,481, Sep. 3, 1987, Pat. No. 4,826,482, which is a continuation-in-part of Ser. No. 22,167, Mar. 5, 1987, Pat. No. 4,808,161, and a continuation-in-part of Ser. No. 836,023, Mar. 4, 1986, Pat. No. 4,778,451.

[51] Int. Cl.⁵ ............................ A61M 1/00; F16L 3/00
[52] U.S. Cl. .................................... 604/151; 604/251; 248/121
[58] Field of Search ............... 604/411, 174, 251, 151; 248/121, 125, 318; 137/561 A, 565

[56] References Cited

U.S. PATENT DOCUMENTS

| | | | |
|---|---|---|---|
| 1,084,753 | 1/1914 | Owens | 604/80 |
| 1,572,043 | 2/1926 | Schellberg | 604/80 |
| 2,065,012 | 12/1936 | Mulford | 248/318 |
| 3,625,211 | 12/1971 | Butler | 128/214 C |
| 3,756,237 | 9/1973 | Chittenden | 128/227 |
| 3,923,279 | 12/1975 | Gresley et al. | 248/318 |
| 4,087,864 | 5/1978 | LaBove et al. | 604/174 X |
| 4,364,387 | 12/1982 | Larkin | 604/411 |
| 4,425,123 | 1/1984 | Di Salvo | 604/247 |
| 4,541,596 | 9/1985 | Price | 248/125 |
| 4,699,296 | 10/1987 | Schrock, Jr. | 222/85 |
| 4,706,368 | 11/1987 | Crissman et al. | 29/526 R |
| 4,725,027 | 2/1988 | Bekavich | 248/125 |
| 4,769,015 | 9/1988 | Bloxom, Jr. | 604/277 |
| 4,787,890 | 11/1988 | Ufermann | 604/411 |
| 4,850,560 | 7/1989 | Ross | 248/295.1 |

Primary Examiner—John Rivell
Attorney, Agent, or Firm—Bromberg & Sunstein

[57] ABSTRACT

A compact intravenous fluid delivery system for intravenous injection of fluid into a patient has in one embodiment a spike, for connection to a fluid supply reservoir whose top and bottom define a vertical interval; a fluid metering device for accepting fluid from the reservoir and for displaying the flow of fluid; a fluid cannula for conveying fluid from the spike to the fluid metering device; a fluid delivery tube for conveying the fluid from the metering device to the patient; and a reservoir mounting frame for mounting the fluid supply reservoir in relation to the metering device so that the metering device is substantially contained within the vertical interval defined by the top and bottom of the reservoir. In a preferred embodiment, an intravenous tube having a length greater than 20 cm provides a conduit for passage of fluid from the fluid reservoir to the metering device. The system may include a pump mounted so that the pump and the metering device are both substantially contained within the vertical interval defined by the top and bottom of the reservoir.

19 Claims, 2 Drawing Sheets

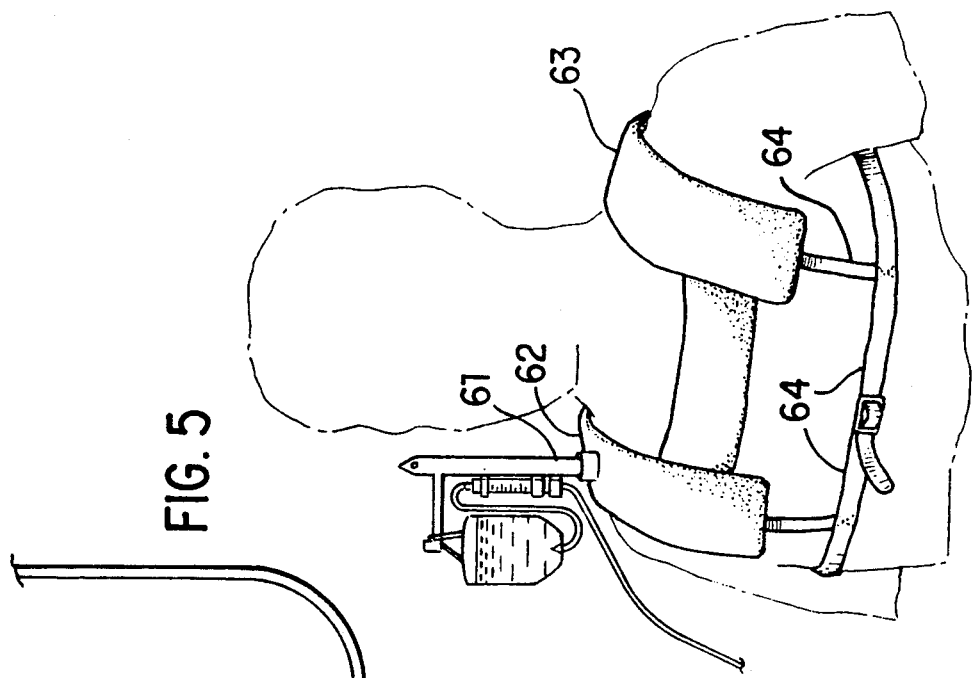
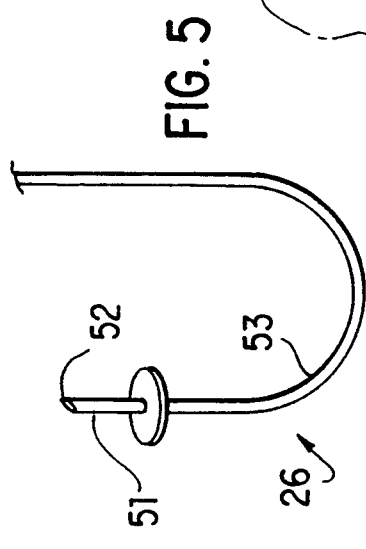
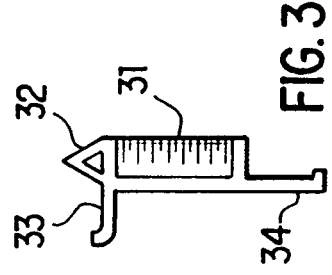
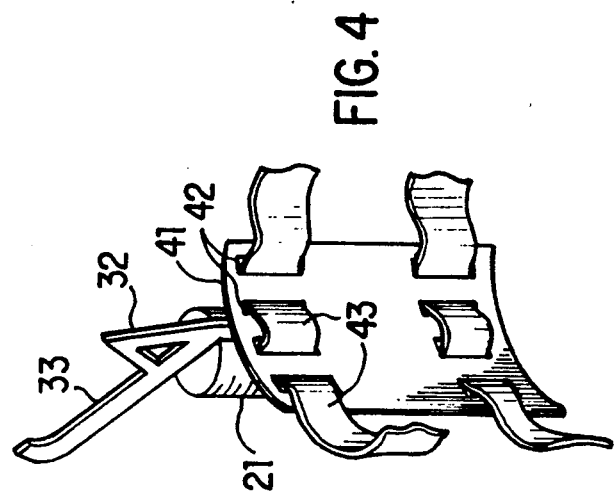

COMPACT INTRAVENOUS FLUID DELIVERY SYSTEM

This application is a continuation-in-part of application Ser. No. 792,483 for Intravenous Fluid Delivery System with Air Elimination by Kamen and Faust, filed Nov. 15, 1991, and application Ser. No. 792,877 for Pump Controller using Acoustic Spectral Analysis by Kamen, Seale, Briggs and Arnold, filed Nov. 15, 1991; application Ser. No. 673,835 filed Mar. 22, 1991 now abandoned (for Constant-Pressure Fluid Supply System); application Ser. No. 615,612 filed Nov. 19, 1990 now abandoned (for Acoustic Volume Measurement with Fluid Management Capability); and application Ser. No. 614,806 filed Nov. 19, 1990 now abandoned (for Integral Intravenous Fluid Delivery Device), which is a continuation-in-part of applications Ser. No. 523,801 filed May 15, 1990 now U.S. Pat. No. 5,088,515 (for a Valve System with Removable Fluid Interface) and Ser. No. 345,387 filed May 1, 1989, issued Dec. 11, 1990, as U.S. Pat. No. 4,976,162 (for an Enhanced Pressure Measurement Flow Control System), which is a continuation-in-part of application Ser. No. 092,481 filed Sep. 3, 1987, issued as U.S. Pat. No. 4,826,482, which is a continuation-in-part of application Ser. No. 022,167 filed Mar. 5, 1987, issued as U.S. Pat. No. 4,808,161, and application Ser. No. 836,023 filed Mar. 4, 1986, issued as U.S. Pat. No. 4,778,451. These related applications are hereby incorporated herein by reference.

TECHNICAL FIELD

The invention relates generally to medical intravenous fluid delivery systems and more specifically to compact systems suitable for ambulatory use.

BACKGROUND OF THE INVENTION

A typical prior-art intravenous (IV) fluid delivery system is shown in FIG. 1. FIG. 1 shows a reservoir 1, which is hung from a pole 2, a volume metering device 3, which is attached to the reservoir 1 by an IV line 4, and a pump 5, which is clamped to the pole 2 and through which the IV line 6 passes. The IV line 4 may consist of a spike attached directly to the metering device 3 or a spike attached to one end of a short intravenous tube, the other end being attached to the metering device 3. The spike itself is a short, straight, plastic tube with its end cut at an angle to form a sharp point capable of penetrating the seal of the reservoir and thereby opening the delivery port. Spikes tubes known in the prior art are typically less than 10 cm (3 or 4 inches) long. Typical prior-art pumps 5 are large, heavy peristaltic pumps, which operate by peristaltic action on the IV tube 6. To enable the patent to walk around, the pole 2 is typically mounted on a base having casters. The weight of the pump 5 by itself makes it difficult for the patient to walk around without the help of a pole mounted on casters; in addition, many prior art pumps must be plugged into a wall socket. The combined height of the reservoir 1, the volume metering device (normally a flexible drip chamber) 3 and the pump 5 is typically 45-90 cm (18-36 inches).

Other prior art support structures for intravenous fluid delivery systems are described in the following four patents.

U.S. Pat. No. 4,850,560 to Ross discloses an adjustable hanger for hanging an intravenous fluid reservoir. The hanger includes an arm having a suspension member, and has an opening for receiving a hanger support frame. A plunger is slidably mounted on the arm, and a biasing element is interposed between the arm and the plunger for biasing the plunger against the support frame for locking the adjustable hanger in a desired position. In a preferred embodiment, the plunger includes a button, the arm includes a finger tab and the suspending member may be in the form of a hook which includes a finger support portion.

U.S. Pat. No. 4,706,368 to Crissman discloses a method for supporting the drip chamber of an apparatus for intravenous fluid delivery that overcomes the problems encountered when the flow sensor and the drip chamber to which it is attached become tilted during use. The method includes mounting the sensor to the support pole with a bracket. The method includes "providing a rigid support bracket having an elongated arm section, a first clamping member adapted to be removably secured to said IV pole, and a second clamping member adapted to be removably secured to said flow chamber."

U.S. Pat. No. 4,699,296 to Schrock discloses a dispensing device for intravenous injection of fluids into a patient comprising a cradle member for supporting a disposable aseptic rectangular package of fluid, a dispensing device including hollow needles for piercing the package to access the fluid, and a level indicator for indicating the amount of fluid in the package. The cradle has a hanger member which in a preferred embodiment is a hook.

U.S. Pat. No. 1,084,753 to Owens discloses an intravenous apparatus which enables the operator to observe and regulate the flow of solution into a vein. The apparatus includes two glass containers, a first container for holding sterilized water and a second container filled with solution to be injected into the vein. A short tube extending upward into the second container protects against the entrance of foreign particles into the needle. An air ingress tube in the bottom of the first container allows bubbles of air to rise visibly through the sterilized water and enter a closed volume defined by the two containers such as to replace solution flowing from the second container. The bubbles provide an indication of solution flow into the vein.

Similar support structures are used for supporting the components of medical fluid delivery systems for other purposes such as proctotherapy. The following five patents describe prior art relevant to the present invention.

U.S. Pat. No. 4,769,015 to Bloxom discloses a mounting assembly for use in the adjustable supporting of various components of a colonic irrigation or flushing apparatus of the type which directs irrigating fluid by gravity. The mounting assembly includes an elongated base having a plurality of connecting elements on which various components, such as the supply container and monitoring device are supported and further, wherein the connecting elements are structured for selective movement and placement thereof along the length of the base so as to properly position the supply container, monitoring device and depending conduit and introduction element in a preferred location relative to one another and the user of the apparatus being treated.

U.S. Pat. No. 4,425,123 to Di Salvo discloses a parenteral liquid application apparatus that provides for controlled application of parenteral fluid to a patient, in which the fluid is supplied from a flexible bag which changes its volume as the fluid is withdrawn therefrom. The apparatus includes a stationary support pole having a support arm at the top of the pole. A reservoir is suspended from the support arm. A drip chamber is mounted directly beneath the reservoir and the drip chamber and a flow stabilization device are mounted to a scale carrier which is slidably and adjustably mounted to the pole.

U.S. Pat. No. 3,756,237 to Chittenden discloses an irrigation solution administration system including a flexible-pouch reservoir positioned for parallel flow of fluid from a solution container and the reservoir to the instrument being used. The reservoir is placed in-line with the tubing connecting the solution container and the delivery instrument by means of a "Y" type connector. Two solution containers may be provided so that as one container is emptied, it can be replaced while flow continues through a second container. Both containers and the reservoir may be suspended from a horizontal pole-mounted arm. Solution flows by gravity and the reservoir assists in maintaining a constant pressure head.

U.S. Pat. No. 3,625,211 to Butler discloses an apparatus for administering to a patient a pre-measured volume of parenteral solution from a prime fluid supply. The apparatus includes a fluid reservoir, a measuring chamber below the reservoir, a drip barrel below the chamber and a two-way valve connected between the measuring chamber and the drip barrel, connected by a tube to the reservoir. The valve arrangement prevents the possibility of the prime fluid supply being connected directly to the patient and enables repeat administration without manipulation of an antiairentrainment valve.

U.S. Pat. No. 1,572,043 to Schellberg discloses a portable apparatus for use in proctotherapy comprising a plurality of holding receptacle flasks, a distribution system including flexible tubes and a multiported distributing valve all supported by a supporting member having a ring-tube body with extended arms adapted to support the flasks, the tubes and the distribution valve. In a preferred embodiment the supporting member stands on a tripod with caster rollers. An irrigation fluid is delivered to the intestine by gravity.

None of the above described systems provides a compact, portable intravenous fluid delivery system such as provided by the present invention.

SUMMARY OF THE INVENTION

A compact intravenous fluid delivery system for intravenous injection of fluid into a patient is provided in one embodiment comprising a spike, for connection to a fluid supply reservoir whose top and bottom define a vertical interval; a fluid metering device for accepting fluid from the reservoir and for displaying the flow of fluid; a fluid cannula for conveying fluid from the spike to the fluid metering device; a fluid delivery tube for conveying the fluid from the metering device to the patient; and a reservoir mounting frame for mounting the fluid supply reservoir in relation to the metering device so that the metering device is substantially contained within the vertical interval defined by the top and bottom of the reservoir. In a preferred embodiment, an intravenous tube having a length greater than 20 cm provides a conduit for passage of fluid from the fluid reservoir to the metering device. The system may include a pump mounted so that the pump and the metering device are both substantially contained within the vertical interval defined by the top and bottom of the reservoir. The system may mount removably and rotatably on a hook or to a pole or may include a carrying handle or straps so it may be carried by the patient. The metering device may be removably mounted to the frame. The frame and the metering device may have integral construction. The pump may include a disposable cassette formed integrally with the fluid delivery tube. The frame may include a battery compartment. The support arm may include a locking mechanism such that the reservoir is constrained from falling when the patient moves.

BRIEF DESCRIPTION OF THE DRAWINGS

FIG. 3 shows a reservoir mounting frame according to a second embodiment of the present invention.

FIG. 4 shows a reservoir mounting frame according to a third embodiment of the present invention.

FIG. 5 shows an intravenous tube attached to a spike.

FIG. 6 shows the frame mounted on a shoulder harness.

DESCRIPTION OF SPECIFIC EMBODIMENTS

The present invention provides a compact IV system that the patient can carry without the use of the caster-mounted pole of the prior art. In a preferred embodiment the system includes a lightweight pump and key components are frame-mounted level with the fluid reservoir.

Figure 2:
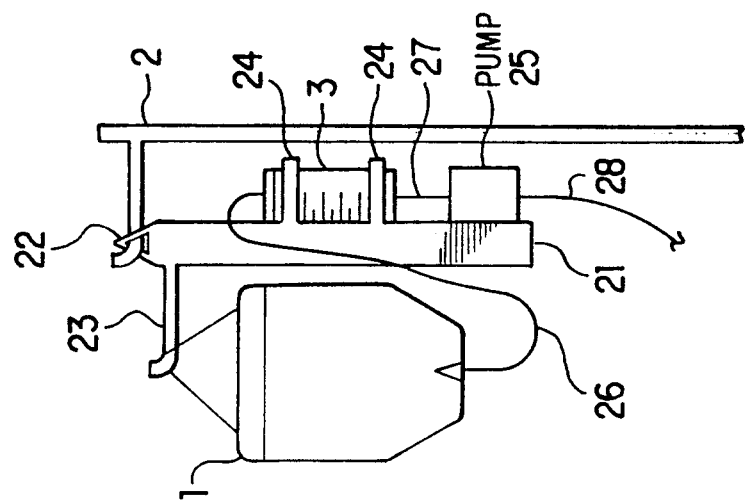
FIG. 2 shows an intravenous fluid delivery system having a reservoir mounting system according to a first embodiment of the present invention.
Figure 1:
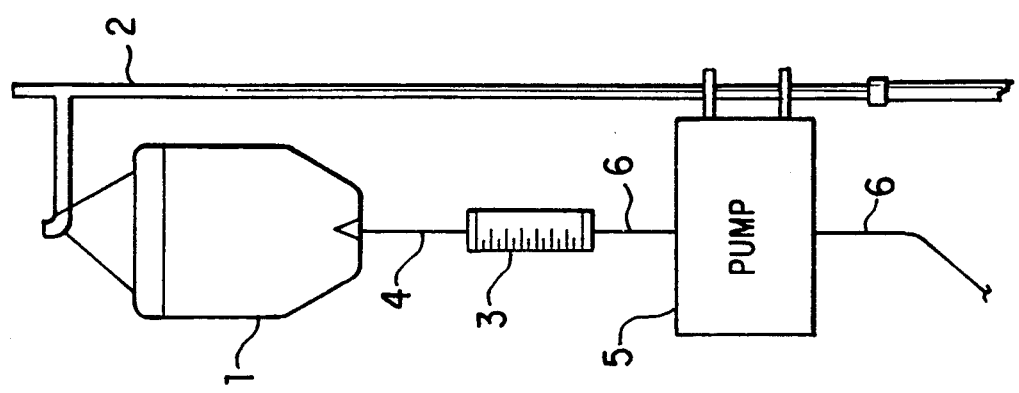
FIG. 1 is a general view of a prior art intravenous fluid delivery system.

The present invention in a first embodiment provides a compact intravenous fluid delivery system as shown in FIG. 2. FIG. 2 shows an IV system using a bracket (or frame) 21 according to the present invention. The bracket 21 has an eye 22 so that it may be hung on a pole 2. The eye 22 may be pivotable so that bracket 21 may be easily turned to put the metering device 3 or the reservoir 1 in a position where they can be easily seen. The bracket 21 also has a hook 23 that the reservoir 1 may hang on. It can be seen that the height of the bracket is approximately the same as the height of the reservoir, and that the reservoir is hung from the top of the bracket. The hook 23 may have a locking mechanism for preventing the reservoir 1 from falling off. The bracket 21 also has grips 24 for removably attaching the metering device 3 (shown in FIG. 2 as a flexible drip chamber). A small pump 25 may be attached to the bracket 21. The pump 25 may be battery-driven, and the batteries may be placed inside the body of the bracket 21.

A portion of the body of the bracket 21 may have a handle formed thereon, so that the patient may carry the bracket 21 and the components that are hung thereon. The bracket 21 may also include a clamp or other means for attachment to a bed rail or pole.

If the drip chamber 3 is to be located within a vertical range defined by the top and bottom of the reservoir 1, a long intravenous tube must be provided for attachment to a conventional spike. Alternatively, there may be provided a preformed spike tube 26, between the drip chamber 3 and the reservoir 1, that is substantially longer and formed to a different shape than the conventional spikes currently in use. The spike tube 26 of a preferred embodiment of the present invention comprises a spike (51 in FIG. 5) having a sharp end 52 capable of penetrating the seal of the reservoir 1, and an intravenous tube 53 attached to the spike. The length of the spike tube of a preferred embodiment of the present invention for use with a typical IV bag, as shown in FIG. 2, is at least 20 cm and, for convenience, approximately equal to the sum of the height and the width of the IV bag, i.e., approximately 35 cm (14 inches).

A metering device 3 is flexible and sealed so that, when connected to a filled reservoir and to a peristaltic or other positive displacement pump, the metering device (i.e. drip chamber) may be primed by squeezing air out via the spike tube through the reservoir and allowing fluid to enter until the metering device is approximately half full of fluid. When the metering device has been primed in this way, the reservoir will continually refill the metering device even when the level of the fluid in the reservoir is below the level of the top of the metering device by virtue of the low pressure in the chamber of the metering device caused by the withdrawal of fluid by the pump.

A disposable "cassette," comprising a rigid housing and a flexible membrane, may be built into the fluid delivery IV line between portions 27 and 28, so that the cassette may be received by the pump 25. This cassette would be in contact with the IV fluid and, therefore, would be disposable along with the rest of the IV line. The cassette allows a smaller, more efficient and more accurate pump 25 to be used instead of the large peristaltic pumps of the prior art, which simply applied peristaltic action to the IV tube. The cassette may be of the type described in several patent applications by the inventor of the present invention, such as Ser. No. 614,806 for an Integral Intravenous Fluid Delivery Device, referred to above. The pump 25 may be a rotary peristaltic pump as described in application Ser. No. 673,834, referred to above.

As an alternative to bracket 21, the metering device (including a flexible drip-tube) 31 shown in FIG. 3 may be given an eye 32 for hanging the metering device directly from the pole 2, and a hook 33 for carrying the reservoir 1. The metering device 31 may a)so include a receptacle 34 to which the pump 25 may be attached. Such a metering device would perform the same function as the bracket 21 described above, allowing the patient to walk around freely.

As a second embodiment of bracket 21, a frame may be provided as shown in FIG. 4. The frame may include support piece 41 with slots 42 for accepting a strap 43 permitting attachment of the system to the patient's upper arm. A third embodiment of the bracket 21 shown in FIG. 6, the frame may include a lower extension 61 and a clamp 62 permitting removable attachment to a semi-rigid shoulder harness 63 having straps 64 so that the system may be carried over the patient's shoulder, freeing the patient's hands.

Instead of the typical IV bags and bottles that are used as reservoirs, a pressurized reservoir may be used. Such pressurized IV reservoirs are well-known and comprise a balloon-like sac inside a rigid housing. The sac is stretched when filled with fluid, thereby imparting pressure to the fluid.

It can be seen from the above description that the present invention provides several advantageous features.

1. The system is compact. The height of the system is not substantially greater than the height of the reservoir.
2. The system is portable. In a preferred embodiment the frame has an eye so the frame can be removably mounted. In another embodiment the frame has a clamp so the system can be pole-mounted. In other embodiments the frame has a handle, a strap or a harness attachment so the system can be conveniently carried by the patient. The frame may include a battery compartment for the pump. The reservoir may be pressurized to facilitate recharge of the drip tube.
3. The system is robust. All elements of the system may be securely attached to the frame. The frame may either include grips for gripping the metering device or the frame and metering device may be integrally constructed. The pump may be directly attached to the frame. The reservoir may be secured by a locking mechanism that prevents the reservoir from falling when the patient moves.
4. The system offers sanitary construction. In a preferred embodiment the wetted portion of pump includes a disposable "cassette".

What is claimed is:

1. A compact intravenous fluid delivery system for intravenous injection of fluid into a patient comprising:
   spike means, for connection to a fluid supply reservoir having a top and a bottom, the top and bottom of the reservoir defining a vertical interval;
   metering means for accepting fluid from the reservoir and for displaying the flow of fluid;
   fluid cannula means for conveying fluid from the spike means to the metering means;
   fluid delivery means for accepting fluid from the metering means and for conveying the fluid to the patient; and
   reservoir mounting means for mounting the fluid supply reservoir in relation to the metering means so that the metering means is substantially contained within the vertical interval defined by the top and bottom of the reservoir.

2. A system according to claim 1, wherein the fluid delivery means includes pump means for pumping the fluid to the patient; and the mounting means includes means for mounting the pump means in relation to the reservoir mounting means and the metering means so that the pump means and the metering means are both substantially contained within the vertical interval defined by the top and bottom of the reservoir.

3. A system according to claim 1, wherein the mounting means includes means for mounting the system removably and rotatably on a hook.

4. A system according to claim 1, further including means for mounting the system removably and rotatably to a pole.

5. A system according to claim 1, further including carrying means for enabling the patient to carry the system.

6. A system according to claim 5, wherein the carrying means includes a handle.

7. A system according to claim 5, wherein the carrying means includes a strap.

8. A system according to claim 5, wherein the carrying means includes means for attachment to a shoulder harness.

9. A system according to claim 1, wherein the reservoir mounting means includes gripping means for gripping the metering means such that the metering means may be removably mounted.

10. A system according to claim 1, wherein the reservoir mounting means and the metering means have integral construction.

11. A system according to claim 1, wherein the pump means includes a removable wetted portion, wherein the removable wetted portion comprises a cassette formed integrally with a tube.

12. A system according to claim 1, wherein the mounting means includes a battery compartment.

13. A system according to claim 1, wherein the mounting means includes a locking mechanism such that the reservoir is constrained from falling off the mounting means when the patient moves.

14. A device for holding intravenous-fluid-delivery components in a compact manner, the device comprising:

a vertical member having a top end;

means, attached to the vertical member, for mounting a fluid supply reservoir having a top and a bottom, the top and bottom of the reservoir defining a vertical interval;

means, attached to the vertical member, for mounting a metering chamber for accepting fluid from the reservoir and for displaying the flow of fluid, the chamber mounting means so that the chamber is substantially contained within the vertical interval defined by the top and bottom of the reservoir, when both the reservoir and the chamber are mounted; and an eye located at the top end of the vertical member so that the vertical member may be hung from a pole.

15. A device according to claim 14, wherein the vertical member, the reservoir mounting means and the chamber mounting means have integral construction.

16. A device according to claim 14, wherein the reservoir mounting means includes a locking mechanism such that the reservoir is constrained from falling off the reservoir means mounting means.

17. A device according to claim 14, further including means, attached to the vertical member, for mounting an intravenous-fluid pump.

18. A device according to claim 17, wherein the vertical member, the reservoir mounting means and the chamber mounting means have integral construction.

19. A device according to claim 17, wherein the reservoir mounting means includes a locking mechanism such that the reservoir is constrained from falling off the reservoir means mounting means.

* * * * *

UNITED STATES PATENT AND TRADEMARK OFFICE
CERTIFICATE OF CORRECTION

PATENT NO. : 5,222,946
DATED : June 29, 1993
INVENTOR(S) : Kamen

It is certified that error appears in the above-indentified patent and that said Letters Patent is hereby corrected as shown below:

col. 7, line 22    after "chamber mounting means" insert
--being located with respect to the
reservoir mounting means--

Signed and Sealed this

Twenty-ninth Day of March, 1994

Attest:

BRUCE LEHMAN

Attesting Officer      Commissioner of Patents and Trademarks